United States Patent [19]

Plessen et al.

[11] Patent Number: 5,081,263
[45] Date of Patent: Jan. 14, 1992

[54] DIOXANE ADDUCTS OF AROMATIC META- OR PARA-HYDROXY-CARBOXLIC ACIDS

[75] Inventors: von Helmold Plessen, Königstein/Taunus; Siegbert Rittner, Mörfelden-Walldorf, both of Fed. Rep. of Germany

[73] Assignee: Hoechst Aktiengesellschaft, Frankfurt am Main, Fed. Rep. of Germany

[21] Appl. No.: 450,402

[22] Filed: Dec. 14, 1989

[30] Foreign Application Priority Data

Dec. 19, 1988 [DE] Fed. Rep. of Germany ....... 3842712

[51] Int. Cl.$^5$ ............................................. C07D 319/12
[52] U.S. Cl. ................................... 549/377; 562/434; 562/467; 562/474; 562/475

[58] Field of Search ................. 549/377; 562/467, 474, 562/475, 434

[56] References Cited

U.S. PATENT DOCUMENTS 4,618,701 10/1986 Neeb et al. ........................... 562/467

*Primary Examiner*—Nicky Chan

[57] ABSTRACT

The invention relates to the dioxane adducts of armoatic meta-or para-hydroxycarboxylic acids, which consist, per mole, of 1 mole of 1,4-dioxane and about 2 moles of hydroxycarboxylic acid. The invention further relates to a process for the preparation of these adducts, which comprises dissolving the hydroxycarboxylic acids in dioxane or a mixture of the latter with water or with an organic solvent and then allowing the adducts to crystallize.

10 Claims, No Drawings

DIOXANE ADDUCTS OF AROMATIC META- OR PARA-HYDROXY-CARBOXLIC ACIDS

A number of aromatic hydroxycarboxylic acids are of great economic importance as organic chemical intermediates. Thus, for example, 3-hydroxy-2-naphthalenecarboxylic acid is widely used as a coupling component for azo dyes, which are used for dyeing textiles. 2-hydroxy-6-naphthalenecarboxylic acid and 4-hydroxybenzoic acid are monomers from which plastics and fibers with outstanding applicational properties can be obtained.

The preparation of hydroxycarboxylic acids of this type in the pure form is frequently associated with difficulties. Known basic processing operations for purifying organic compounds, such as distillation, sometimes fail in the case of aromatic hydroxycarboxylic acids, because these compounds undergo intermolecular esterification or decarboxylation when relatively high temperatures are used. Crystallization likewise frequently fails as a purification process, because the compounds are too sparingly soluble or because impurities are entrapped during crystal formation. Thus, for example, for the reasons given, 2-hydroxy-6-naphthalenecarboxylic acid cannot be distilled and its purification by crystallization from solvents presents difficulties due to persistently adhering accompanying substances (European Patent 81,753).

Surprisingly, it has now been found that the formation of adducts between aromatic hydroxycarboxylic acids, in which the hydroxyl group and the carboxyl group are in the meta- or para-position relative to each other, and 1,4-dioxane offers the possibility of purifying hydroxycarboxylic acids of this type. Moreover, the adducts comprising the hydroxycarboxylic acids and dioxane can also be used as novel compounds or as intermediates.

The invention relates to these adducts themselves, and furthermore to a process for their preparation.

The process for the preparation of adducts of aromatic meta- or para-hydroxycarboxylic acids and 1,4-dioxane comprises dissolving the hydroxycarboxylic acids in 1,4-dioxane or a mixture of the latter with water or with an organic solvent, and then allowing the adducts to crystallize.

The adducts of the aromatic hydroxycarboxylic acids and dioxane have the general formula

in which $R_1$ and $R_2$ denote hydrogen, fluorine, chlorine, bromine or a nitro group and Ar denotes the benzene or naphthalene radical. The particular feature of the said adducts is that hydrogen bridge bonds exist between the hydroxyl groups of the aromatic compounds and the oxygen atoms of the dioxane, so that the adducts are 2:1 adducts.

The carboxyl groups of two hydroxycarboxylic acid molecules are, in turn, dimerized, so that relatively long chain-like arrangements can form.

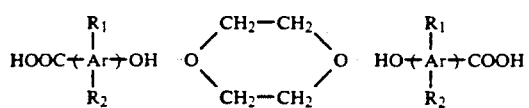

Industrially produced aromatic meta- or para-hydroxycarboxylic acids can be used directly to prepare the adducts.

Preferably, the hydroxycarboxylic acids are dissolved in a mixture of 1,4-dioxane and water having a dioxane content of 20-90% by weight, with heating, and the adducts are then allowed to crystallize out, with cooling. The crystallized product is, for example, filtered off and dried in vacuo in a stream of nitrogen.

Instead of a mixture of dioxane with water, it is also possible to use a mixture of dioxane with an organic solvent. It is even possible to use water and water-miscible organic solvents simultaneously as mixture components; for example, the dioxane adduct can be allowed to crystallize out from ternary mixtures of dioxane/water/lower alcohols or dioxane/water/polyethylene glycols. Generally, the dioxane content of the mixtures with water and/or organic solvents is at least 10% by weight, preferably at least 20% by weight, and in particular at least 30% by weight.

However, it is also possible initially to dissolve the hydroxycarboxylic acids in dioxane and then to add water or organic solvents to this solution in an amount such that crystallization of the adducts occurs. Moreover, it is possible to distill off dioxane from solutions of the hydroxycarboxylic acids in dioxane or mixtures of dioxane with water or organic solvents, in an amount such that crystallization occurs.

The crystallization of the adducts can be carried out not only at room temperature, but also at elevated (up to the boiling point) or reduced temperatures (down to about −20° C.). Crystallization is also possible at elevated pressure, with a corresponding rise in the boiling point.

The crystallization of the adducts can be carried out not only discontinuously, but also continuously. Here, it is possible to employ crystallization with cooling or with evaporation or the so-called vacuum crystallization. In these cases, it can be advantageous to operate under an inert gas atmosphere. Nitrogen is particularly suitable here as the inert gas. Carbon dioxide or argon may also be used for this purpose.

The following hydroxycarboxylic acids are particularly suitable for the adduct preparation according to the invention:
4-hydroxybenzoic acid
3-nitro-4-hydroxybenzoic acid
2-hydroxy-6-naphthalenecarboxylic acid
3-chloro-4-hydroxybenzoic acid The following organic solvents or combinations of these can, for example, be mixed with the dioxane in the process according to the invention:
Aliphatic hydrocarbons, for example those having 5 to 10 carbon atoms
Aromatic hydrocarbons, such as benzene, toluene, xylene and cumene
Alicyclic hydrocarbons, such as cyclohexane, decalin and tetralin
Chlorinated hydrocarbons, such as $CCl_4$, $CHCl_3$, $CH_2Cl_2$, dichloroethanes and trichloroethylene
Esters, for example esters of acetic acid, in particular ethyl acetate
Alcohols, for example those having 1 to 8 carbon atoms.

In comparison with the free hydroxycarboxylic acids, the adducts have markedly altered solubilities and can readily be recrystallized.

The dioxane can be separated off again from the adducts according to the invention by various chemical operations and the underlying hydroxycarboxylic acids can thus be recovered in highly pure form.

For example, the dioxane is virtually completely split off by heating the adducts to about 100° C. in vacuo. In some cases, the dioxane is so loosely bound in the adduct that temperatures of 30°–50° C. are already sufficient, with the application of vacuum, to recover the dioxane-free hydroxycarboxylic acid.

It is also possible to obtain the dioxane-free hydroxycarboxylic acids by recrystallising the adducts from another solvent, for example dilute ethanol. Moreover, dioxane-free hydroxycarboxylic acids can be obtained by dissolving the corresponding adducts in sodium hydroxide solution and subsequently precipitating with dilute mineral acid.

A further possibility for splitting off dioxane from the adducts according to the invention and obtaining the underlying hydroxycarboxylic acids comprises subjecting the adduct to steam distillation. It is also possible to mix the adduct with a suitable solvent, for example with a ketone, and to distill off solvent from the mixture until the dioxane has been removed. The hydroxycarboxylic acid can be isolated from the solution by cooling and filtration or by concentrating the solution.

Formation of the adduct and subsequent liberation of the hydroxycarboxylic acids is particularly suitable for purifying those aromatic hydroxycarboxylic acids which are used as precursors for the preparation of dyes or plastics. Of particular importance, for example, are the adducts of 4-hydroxybenzoic acid and 2-hydroxy-6naphthalenecarboxylic acid: the highly pure hydroxycarboxylic acids obtained from the two adducts can be reacted together to form highly pure polyesters, from which valuable plastics or fibers can be produced (U.S. Pat. No. 4,393,191).

It is surprising that 2:1 adducts are formed since, in view of the hydrogen bridges (chelates) which are known from the aromatic o-hydroxycarboxylic acids,

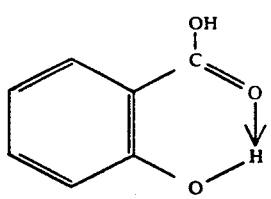

formation of intermolecular bonds, for example, in the case of p-hydroxybenzoic acids, was to be expected.

The percentage data given in the following examples are percentages by weight.

EXAMPLE 1

12.5 g of 4-hydroxybenzoic acid were dissolved in 90 g of dioxane with stirring and heating. 68 g of n-heptane were added to the solution and the mixture was heated until dissolution was complete. The solution was then allowed to cool slowly and the product to crystallize out. After 20 h, the well-formed, columnar crystals were filtered off.

X-ray structural analysis of a single crystal gave the following formula for the crystal

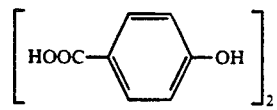

EXAMPLE 2

20 g of 4-hydroxybenzoic acid were dissolved in 150 g of dioxane. The solution was evaporated to dryness in vacuo at 50° C. (bath). The yield was 26.0 g of the 2:1 adduct.

EXAMPLE 3

30 g of 3-nitro-4-hydroxybenzoic acid were dissolved with 100 g of dioxane and 100 g of water, with heating and stirring. The solution was treated with 2.5 g of activated charcoal and then filtered whilst hot. After slow cooling, the crystallized product was filtered off and dried in vacuo over concentrated sulfuric acid. 28.7 g of the 2:1 adduct were obtained.

X-ray structural analysis of a single crystal gave the formula

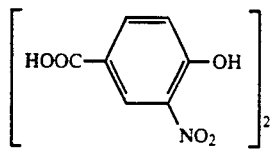

Found: C 47.3/47.4%; H 3.7/3.8%;
Calculated: C 47.58%; H 3.96%.

EXAMPLE 4

50 g of a crude 2-hydroxy-6-naphthalenecarboxylic acid (obtained by the Kolbe-Schmitt reaction) were dissolved in a mixture of 400 g of water and 300 g of dioxane with stirring and heating. After mixing with 5 g of activated charcoal, the mixture was filtered. The solution was allowed to cool slowly.

The crystallized product was filtered off and washed with 30% strength by weight dioxane. The product was then again recrystallized from a mixture of 360 g of water and 270 g of dioxane. The pure product was dried in vacuo over concentrated sulfuric acid.

X-ray structural analysis of a single crystal gave the following structure for the crystal:

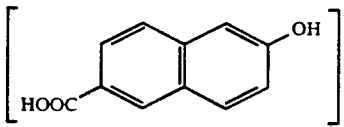

The following table shows the content of impurities for two different starting materials (crude acids) and the corresponding end products (purified acids).

| | | Content of impurities in starting material and end product (% by weight) | | | | |
|---|---|---|---|---|---|---|
| | | 2-Hydroxy-naphthalene-3,6-dicarboxylic acid | 2-Hydroxy-3-naphthalene-carboxylic acid | 2-Naphthol | 2,2'-Dihydroxy-1,1'-dinaphthyl | Color index |
| Example 7 | Starting material | 0.421 | 0.227 | 0.065 | 0.018 | $21.0 \times 10^{-6}$ |
| | End product | 0.018 | <0.05 | <0.05 | <0.05 | $<1.8 \times 10^{-6}$ |
| Example 8 | Starting material | 1.762 | 0.719 | 0.225 | <0.05 | $60.9 \times 10^{-6}$ |
| | End product | 0.085 | <0.05 | <0.014 | <0.05 | $1.8 \times 10^{-6}$ |

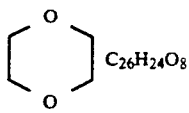

Found C 67.15%; H 5.2%; Dioxane 17.1/17.7%; Calculated: C 67.24%; H 5.17%; Dioxane 19.0%.

EXAMPLE 5

4.24 g of the 2:1 adduct which had been obtained according to Example 4 were mixed with 50 g of water and dissolved with 21 ml of 1N sodium hydroxide solution. After adding a further 50 g of water, the product was precipitated with 22 ml of 1N sulfuric acid with stirring. After filtering off the 2-hydroxy-6-naphthalenecarboxylic acid, washing it with water and drying it in vacuo over concentrated sulfuric acid, a yield of 3.42 g was obtained. The dioxane content was 20 ppm.

EXAMPLE 6

5.3 g of the 2:1 adduct which had been obtained according to Example 4 were stirred into 100 g of water. The suspension was heated to the boil and 20 g of water were distilled off therefrom. After cooling, 16.1 g of butanone were added to the mixture. The mixture was then heated again and butanone and 25 g of water were distilled off. After cooling off the mixture, the product was filtered off, washed and dried in vacuo. Yield: 4.3 g of 2-hydroxy-6-naphthalenecarboxylic acid having a dioxane content of 1 ppm.

EXAMPLES 7 AND 8

50 g of crude 2-hydroxy-6-naphthalenecarboxylic acid (obtained by the Kolbe-Schmitt reaction) were dissolved in a mixture of 400 g of water and 300 g of 1,4-dioxane, with stirring and heating. After mixing with 5 g of activated charcoal, the mixture was filtered. The solution was allowed to cool slowly. The crystals of the adduct separated off were filtered off and washed with 30% strength by weight dioxane. The adduct was then recrystallized, namely from a mixture of 360 g of water and 270 g of dioxane. The product was dried in vacuo over concentrated sulfuric acid. Melting point (after recrystallization from dilute ethanol): 247°-248° C.

| Analysis: | C | H |
|---|---|---|
| calculated | 67.24% | 5.2% |
| found | 67.15% | 5.2% |

EXAMPLE 9

12.5 g of crude 2-hydroxy-6-naphthalenecarboxylic acid were dissolved in a mixture of 42 g of glacial acetic acid and 41 g of dioxane, with stirring and heating. After mixing with 1 g of activated charcoal, the mixture was stirred for 2 min and then filtered. The crystalline adduct separated out from the solution on slow cooling and was filtered off and washed with 20% strength by weight ethanol. Drying in vacuo over concentrated sulfuric acid gave 11.3 g of the adduct.

We claim:

1. A process for the preparation of a dioxane adduct of an aromatic hydroxycarboxylic acid of the formula $(R_1)(R_2)(OH)Ar\text{---}COOH$ wherein $R_1$ and $R_2$ denote hydrogen, fluorine, chlorine, bromine or a nitro group and Ar denotes a benzene or napthalene nucleus, with the proviso that when Ar is a benzene nucleus the OH group is meta or para to the COOH group, and when Ar is a naphthalene nucleus the OH is in the 2-position and the COOH group is in the 6-position, which process comprises dissolving the aromatic hydroxycarboxylic acid in 1,4-dioxane or a mixture of 1,4-dioxane with water, with an organic solvent, or with a combination of water and an organic solvent, and then causing or allowing the resulting adduct to crystallize.

2. The process as claimed in claim 1, wherein the aromatic hydroxycarboxylic acid is dissolved in a mixture comprising 1,4-dioxane and water.

3. The process as claimed in claim 2, wherein the water is included in said mixture in combination with a water-miscible organic solvent, and said mixture is essentially a ternary mixture of 1,4-dioxane/water/lower alcohol or 1,4-dioxane/water/polyethylene glycol.

4. The process as claimed in claim 2, wherein the 1,4-dioxane content of said mixture is at least 10% by weight.

5. The process as claimed in claim 2, wherein the aromatic hydroxycarboxylic acid is dissolved, with heating, in a mixture of essentially 1,4-dioxane and water having a 1,4-dioxane content of 20-90% by weight, and the resulting adduct is then allowed to crystallize out with cooling.

6. The process as claimed in claim 1, wherein Ar denotes a benzene nucleus, hence the aromatic hydroxycarboxylic acid is an aromatic meta- or para-hydroxycarboxylic acid.

7. The process as claimed in claim 6, wherein the aromatic meta- or para-hydroxycarboxylic acid is 4-hydroxybenzoic acid, 3-nitro-4-hydroxybenzoic acid, or 3-chloro-4-hydroxybenzoic acid.

8. The process as claimed in claim 1, wherein Ar denotes a naphthalene nucleus, and wherein the aromatic hyroxycarboxylic acid is 2-hydroxy-6-naphthalenecarboxylic acid.

9. A process for the preparation of a dioxane adduct of 2-hydroxy-6-naphthalenecarboxylic acid, which consists essentially per mole, of 1 mole of 1,4-dioxane and about 2 moles of 2-hydroxy-6-naphthalenecarboxylic acid, which comprises dissolving 2-hydroxy-6naphthalenecarboxylic acid in 1,4-dioxane or a mixture of the latter with water or with an organic solvent and then allowing the adduct to crystallize.

10. The process as claimed in claim 9, wherein 2-hydroxy-6-naphthalenecarboxylic acid is dissolved in a mixture of 1,4-dioxane and water having a dioxane content of 20-90% by weight, with heating, and the adduct is then allowed to crystallize out with cooling.

* * * * *